US006806369B2

United States Patent
Aubart et al.

(10) Patent No.: US 6,806,369 B2
(45) Date of Patent: Oct. 19, 2004

(54) PEPTIDE DEFORMYLASE INHIBITORS

(75) Inventors: Kelly M. Aubart, King of Prussia, PA (US); Siegfried B. Christensen, IV, King of Prussia, PA (US); Jacques Briand, King of Prussia, PA (US); Maxwell David Cummings, Strafford, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/275,522

(22) PCT Filed: May 4, 2001

(86) PCT No.: PCT/US01/14593
§ 371 (c)(1),
(2), (4) Date: Nov. 5, 2002

(87) PCT Pub. No.: WO01/85170
PCT Pub. Date: Nov. 15, 2001

(65) Prior Publication Data
US 2004/0053932 A1 Mar. 18, 2004

Related U.S. Application Data

(60) Provisional application No. 60/201,943, filed on May 5, 2000, and provisional application No. 60/238,084, filed on Oct. 4, 2000.

(51) Int. Cl.$^7$ .................... C07D 217/00; C07D 217/06; C07D 217/12
(52) U.S. Cl. ........................ 546/146; 544/408; 546/113; 548/187; 548/213; 548/225; 548/243; 548/319.5
(58) Field of Search ............................... 546/113, 146; 544/408; 548/187, 213, 225, 243, 319.5

(56) References Cited

U.S. PATENT DOCUMENTS 3,282,986 A 11/1966 Kaczka

FOREIGN PATENT DOCUMENTS

WO   WO 87 04152 A   7/1987

OTHER PUBLICATIONS

Miyagishima, T. et al.: "Further studies on syntheisis and antimicrobial activity of thioformin analogues", Chem. Pharm. Bull., vol. 22, No. 10, 1974, pp. 2283–2287, XP009008360.

*Primary Examiner*—Bernard Dentz
(74) *Attorney, Agent, or Firm*—Soma G. Simon; Mary McCarthy; Charles M. Kinzig

(57) ABSTRACT

PDF inhibitors and novel methods for their use are provided.

3 Claims, No Drawings

PEPTIDE DEFORMYLASE INHIBITORS

This is a 371 of International Application PCT/US01/14593, filed May 4, 2001, which claims benefit from Provisional Applications: 60/201,943, flied May 5, 2000 and 60/238,084, filed Oct. 4, 2000.

FIELD OF THE INVENTION

The present invention relates to the use of novel anti-bacterial compounds, and pharmaceutical compositions containing these, compounds as peptide deformylase inhibitors.

BACKGROUND OF THE INVENTION

Bacterial initiator methionyl tRNA is modified by methionyl tRNA formyltransferase (FMT) to produce formyl-methionyl tRNA. The formyl methionine (f-met) is then incorporated at the N-termini of newly synthesized polypeptides. Polypeptide deformylase (PDF or Def) then deformylates primary translation products to produce N-methionyl polypeptides. Most intracelluar proteins are further processed by methionine amino peptidase (MAP) to yield the mature peptide and free methionine, which is recycled. PDF and MAP are both essential for bacterial growth, and PDF is required for MAP activity. This series of reactions is referred to as the methionine cycle (Figure 1)

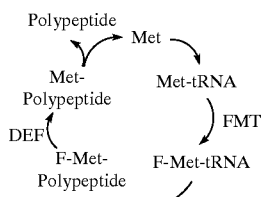

Figure 1. The methionine cycle.

To date, polypeptide deformylase homologous genes have been found in bacteria, in chloroplast-containing plants, in mice and in humans. The plant proteins are nuclear encoded but appear to carry a chloroplast localisation signal. This is consistent with the observation that chloroplast RNA and protein synthesis processes are highly similar to those of eubacteria. No information on protein expression of mammalian PDF gene homologs or functional role for such proteins has been demonstrated to date (Meinnel T. 2000, Parasitology Today, 16(4), 165–168).

Polypeptide deformylase is found in all eubacteria for which high coverage genonic sequence information is available. Sequence diversity among PDF homologs is high, with as little as 20% identity between distantly related sequences. However, conservation around the active site is very high, with several completely conserved residues, including one cyteine and two histidines which are required to coordinate the active site metal (Meinnel, T. et al, 1997, Journal of Molecular Biology, 267, 749–761).

PDF is recoginzed to be an attractive anti-bacterial target, as this enzyme has been demonstrated to be essential for bacterial growth in vitro (Mazel, D. et al, EMBO J. 13 (4), 914–923, 1994), is not involved in eukaryotic protein synthesis (Rajagopalan et al, J. Am. Chem. Soc. 119, 12418–12419, 1997), and is universally conserved in prokaryotes (Kozak, M. Microbiol. Rev. 47, 1–45, 1983). Therefore PDF inhibitors can potentially serve as broad spectrum anti-bacterial agents.

SUMMARY OF THE INVENTION

The present invention involves novel anti-bacterial compounds represented by Formula (I) hereinbelow and their use as PDF inhibitors.

The present invention further provides methods for inhibiting PDF in an animal, including humans, which comprises administering to a subject in need of treatment an effective amount of a compound of Formula (I) as indicated hereinbelow.

DETAILED DESCRIPTION OF THE INVENTION

The compounds useful in the present methods are selected from Formula (I) hereinbelow:

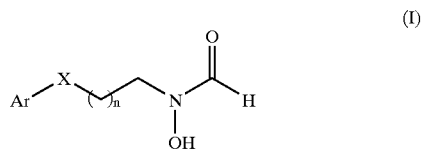

wherein:

X is C or O;

n is 1 or 2

Ar is an aryl group selected from the group consisting of phenyl, azaindolyl, pyridyl, indolyl, quinolinyl, pyrazinyl, benzenethiophenyl, isoxazolyl, isoquinolinyl, napthyl, oxazolyl, isothiazolyl, benzothiaphenyl, furyl, pyridazinyl, thienyl, benzofuryl, imidazolyl, and thiazolyl; such that Ar may be optionally substituted with one, two, or three substituents selected from the group consisting of optionally substituted alkyl or cycloalkyl of one to nine carbons, halo, alkoxy of one to nine carbons, hydroxy, amino, hydroxyalkyl of one to nine carbons, alkoxyalkyl, wherein the alkyl and alkylene groups are independently of one to nine carbons, optionally substituted aryl or optionally substituted heteroaryl, azaindolyl, carboxy, and alkoxycarbonyl.

As used herein, "alkyl" refers to an optionally substituted hydrocarbon group joined together by single carbon-carbon bonds. The alkyl hydrocarbon group may be linear, branched or cyclic, saturated or unsaturated. Preferably, the group is linear. Preferably, the group is unsubstituted. Preferably, the group is saturated. Preferred alkyl moieties are $C_{1-4}$ alkyl, most preferably methyl.

As used herein, "aryl" refers to an optionally substituted aromatic group with at least one ring having a conjugated pi-electron system, containing up to two conjugated or fused ring systems. "Aryl" includes carbocyclic aryl, heterocyclic aryl and biaryl groups, all of which may be optionally substituted. Preferred aryl moieties are phenyl or naphthyl, unsubstituted, monosubstituted, disubstituted or trisubstituted.

Preferred compounds useful in the present invention are selected from the group consisting of:
N-Formyl-N-hydroxy-2-[3-(5-azaindole)phenoxy]ethylamine
N-Formyl-N-hydroxy-2-(7-quinolinoxy)ethylamine
N-Formyl-N-hydroxy-2-(5-isoquinolinoxy)ethylamine
N-Formyl-N-hydroxy-3-phenylpropylamine
N-Formyl-N-hydroxy-4-phenylbutylamine
N-Formyl-N-hydroxy-3-(3-methyl-2-pyridyl)propylamine
N-Hydroxy-(2-phenoxyethyl)formamide
N-Formyl-N-hydroxy-2-(2-trifluoromethylphenoxy)ethylamine
N-Formyl-N-hydroxy-2-(3-bromophenoxy)ethylamine
N-Formyl-N-hydroxy-2-(2-benzyloxyphenoxy)ethylamine
N-Formyl-N-hydroxy-2-(3-chloro-4-fluorophenoxy)ethylamine
N-Formyl-N-hydroxy-2-(3,5-dichlorophenoxy)ethylamine N-Formyl-N-hydroxy-2-(2,3-dichlorophenoxy)ethylamine N-Formyl-N-hydroxy-2-[4-(3-methylpropionate)phenoxy]ethylamine N-Formyl-N-hydroxy-2-(4-acetylphenoxy)ethylamine N-Formyl-N-hydroxy-2-(4-chloro-3-methylphenoxy)ethylamine; and N-Formyl-N-hydroxy-2-(3-chloro-4-methylphenoxy)ethylamine.

N-Formyl-N-hydroxy-2-(napthalen-1-yloxy)ethylamine

N-Formyl-N-hydroxy-2-(napthalen-2-yloxy)ethyl amine

N-Formyl-N-hydroxy-2-(2,4,5-trifluorophenoxy)ethylamine

N-Formyl-N-hydroxy-2-(2-chlorophenoxy)ethylamine

N-Formyl-N-hydroxy-2-(3-hydroxyphenoxy)ethylamine

Also included in the present invention are pharmaceutically acceptable salts and complexes. Preferred are the hydrochloride, hydrobromide and trifluoroacetate salts. The compounds of the present invention may contain one or more asymmetric carbon atoms and may exist in racemic and optically active forms. All of these compounds and diastereomers are contemplated to be within the scope of the present invention.

Compounds of the formula I may be prepared according to the following representative schemes, which are illustrative of the methods employed and are not intended to limit the scope of the invention as defined in the appended claims. Compounds of the formula I wherein X=C, O can be prepared by a procedure analogous to Scheme 1.

Scheme 1

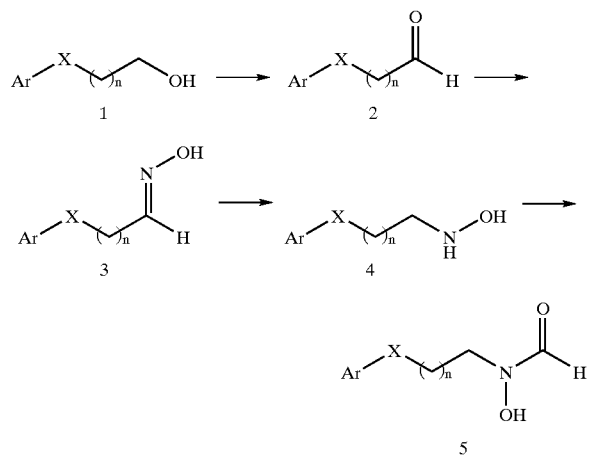

Aryl aldehydes 2-Scheme-1 may be prepared from the aryl alcohols 1-Scheme-1 by conventional means such as oxidation under Swern conditions. Formation of the oxime 3-Scheme-1 is accomplished by treatment of the aldehyde with hydroxylamine hydrochloride in a solvent such as pyridine. The hydroxylamine 4-Scheme-1 is prepared by reduction of the oxime with sodium cyanoborohydride under acidic conditions. Finally N-formyl-N-hydroxylamine 5-Scheme-1 is obtained by treatment of the hydroxylamine with the mixed anhydride formed from formic acid and acetic anhydride in a solvent such as dichloromethane.

Scheme 2

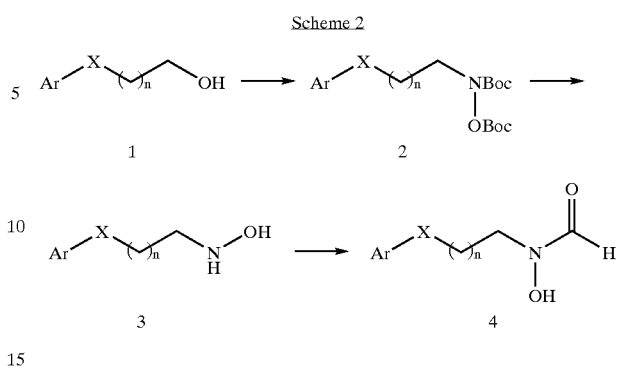

Alternatively, compounds of formula I wherein X=O, C can be prepared by a procedure analogous to Scheme 2. Treatment of aryl alcohol 1-Scheme-2 with tert-butyl N-(tert-butoxycarbonyloxy)carbamate under Mitsunobu conditions provides di-protected hydroxylamine 2-Scheme-2. Deprotection with TFA in CH$_2$Cl$_2$ followed by formylation of the amine as described for Scheme 1 provides N-formyl-N-hydroxylamines 4-Scheme-2.

Alternatively, compounds of formula I wherein X=O can be prepared by a novel solid phase method as shown in Scheme-3. Oxime 2-Scheme-3 can be prepared by treatment of aldehyde 1-Scheme-3 with hydroxylamine hydrochloride in a solvent such as pyridine. Reduction of the oxime using sodium cyanoborohydride under acidic conditions provides hydroxylamine 3-Scheme-3, and formylation using the mixed anhydride prepared from formic acid and acetic anhydride provides N-formyl-N-hydroxylamine 4-Scheme-3. The N-formyl-N-hydroxylamine 4-Scheme-3 is then loaded onto 2-chloro-trityl resin using a base such as triethylamine in a solvent such as dichloromethane. Resin-bound 5-Scheme-3 is then deprotected using tetrabutylammonium fluoride in tetrahydrofuran, providing 6-Scheme-3. Treatment of the free hydroxyl with aromatic alcohols under Mitsunobu conditions, followed by cleavage from the resin (5% TFA/dichloromethane) provides aryl N-formyl-N-hydroxylamines 8-Scheme-3.

Scheme 3

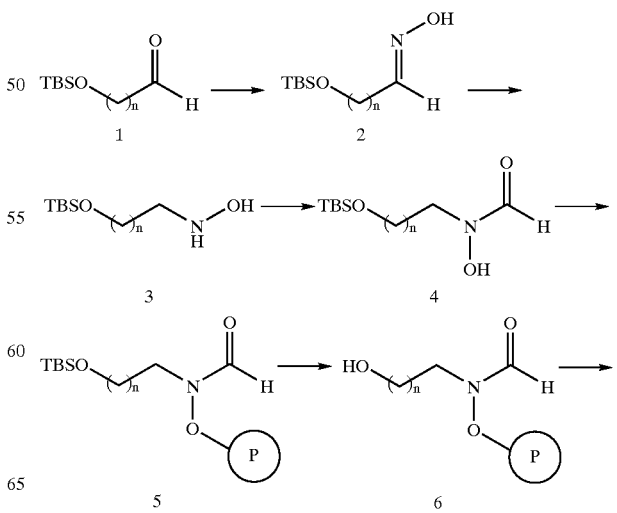

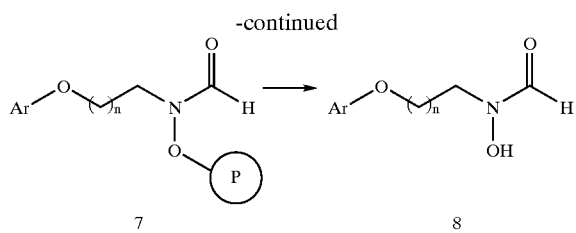

With appropriate manipulation and protection of any chemical functionality, synthesis of the remaining compounds of Formula (I) is accomplished by methods analogous to those above and to those described in the Experimental section.

In order to use a compound of the Formula (I) or a pharmaceutically acceptable salt thereof for the treatment of humans and other mammals it is normally formulated in accordance with standard pharmaceutical practice as a pharmaceutical composition.

The present compounds are useful for the treatment of bacterial infections including but not limited to respiratory tract infections and/or Gram positive infections.

Compounds of Formula (I) and their pharmaceutically acceptable salts may be administered in a standard manner for antibiotics, for example orally, parenterally, sublingually, dermally, transdermally, rectally, via inhalation or via buccal administration.

Compositions of Formula (I) and their pharmaceutically acceptable salts which are active when given orally can be formulated as syrups, tablets, capsules, creams and lozenges. A syrup formulation will generally consist of a suspension or solution of the compound or salt in a liquid carrier for example, ethanol, peanut oil, olive oil, glycerine or water with a flavoring or coloring agent. Where the composition is in the form of a tablet, any pharmaceutical carrier routinely used for preparing solid formulations may be used. Examples of such carriers include magnesium stearate, terra alba, talc, gelatin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils, and are incorporated in a soft gelatin capsule shell.

Typical parenteral compositions consist of a solution or suspension of a compound or salt in a sterile aqueous or non-aqueous carrier optionally containing a parenterally acceptable oil, for example polyethylene glycol, polyvinylpyrrolidone, lecithin, arachis oil or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogs.

Typical dermal and transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg/Kg, of a compound of Formula(I) or a pharmaceutically acceptable salt thereof calculated as the free acid. Each dosage unit for intranasal administration contains suitably 1–400 mg and preferably 10 to 200 mg per person. A topical formulation contains suitably 0.01 to 5.0% of a compound of Formula (I).

The daily dosage regimen for oral administration is suitably about 0.01 mg/Kg to 40 mg/Kg, of a compound of Formula(I) or a pharmaceutically acceptable salt thereof calculated as the free acid. The daily dosage regimen for parenteral administration is suitably about 0.001 mg/Kg to 40 mg/Kg, of a compound of Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the present invention are administered in accordance with the present invention.

The biological activity of the compounds of Formula (I) are demonstrated by the following test:

Biological Assay

S. Aureus or E. Coli PDF activity is measured at 25° C., using a continuous enzyme-linked assay developed by Lazennec & Meinnel, (1997) "Formate dehydrogenase-coupled spectrophotometric assay of peptide deformylase" Anal. Biochem. 244, pp. 180–182, with minor modifications. The reaction mixture is contained in 50 uL with 50 mM potassium phosphate buffer (pH7.6), 15 mM NAD, 0.25 U formate dehydrogenase. The substrate peptide, f-Met-Ala-Ser, is included at the $K_M$ concentration. The reaction is triggered with the addition of 10 nM PDF (Def1) enzyme, and absorbance is monitored for 20 min at 340 nm.

Antimicrobial Activity Assay

Whole-cell antimicrobial activity was determined by broth microdilution using the National Committee for Clinical Laboratory Standards (NCCLS) recommended procedure, Document M7-A4, "Methods for Dilution Susceptibility Tests for Bacteria that Grow Aerobically" (incorporated by reference herein). The compound was tested in serial two-fold dilutions ranging from 0.06 to 64 mcg/ml. A panel of 12 strains were evaluated in the assay. This panel consisted of the following laboratory strains: *Staphylococcus aureus* Oxford, *Streptococcus pneumoniae* R6, *Streptococcus pyogenes* CN10, *Enterococcus faecalis* I, *Haemophilus influenzae* Q1, *Escherichia coli* DC0, *E. coli* EES, *E. coli* 7623 (AcrAB+) *E. coli* 120 (AcrAB−) *Klebsiella pneumoniae* E70, *Pseudomonas aeruginosa* K799wt and *Candida albicans* GRI 681. The minimum inhibitory concentration (MIC) was determined as the lowest concentration of compound that inhibited visible growth. A mirror reader was used to assist in determining the MIC endpoint.

The following examples are illustrative but not limiting of the embodiments of the present invention.

N-Formyl-N-hydroxy-4-phenylbutylamine

1a. To a solution of 4-phenylbutanol (1 g) in dichloromethane (35 mL) at 0° C. was added PDC (7.5 g). The resulting suspension was stirred for 2 h at room temperature. The reaction solution was then filtered through a pad of silica gel. Concentration of the filtrate and flash chromatography of the residue (20% ethyl acetate/hexanes) provided 4-phenylbutanal (237 mg) as a colorless oil.

1b. A solution of 4-phenylbutanal (237 mg) in pyridine (3 mL) was treated with hydroxyamine hydrochloride (134 mg) and stirred overnight. The reaction solution was diluted with dichloromethane and washed with 1M HCl. The organics were dried and concentrated to provide the oxime (259 mg) as a 1:1 mixture of cis and trans isomers as a colorless oil.

1c. To a solution of the above oxime (259 mg) in methanol (10 mL) at 0° C. was added 2 mg of methyl orange. With stirring, sodium cyanoborohydridic (130 mg) was added slowly while simultaenously adding a solution of 6M HCl/methanol (1/1) dropwise as necessary to maintain the pink color of the methyl orange indicator. After stirring at 0° C. for 1 hr, the reaction was brought to pH 9 with 6M NaOH, and the reaction was extracted with dichloromethane. The organics were dried and concentrated to provide the hydroxylamine (244 mg) as a colorless oil.

1d. A solution of the above hydroxylamine (244 mg) acetic anhydride (750 mg), and formic acid (8 mL) was stirred at room temperature for 2 h. The reaction was extractively purified using ethyl acetate and aqueous sodium bicarbonate. The organics were dried and concentrated, and the residue was purified by reverse-phase HPLC to provide N-formyl-N-hydroxy-4-phenylbutylamine, as a colorless oil.

Proceeding in a similar manner, but substituting appropriate intermediates for those described above, the following compounds were made:

N-Formyl-N-hydroxy-3-phenylpropylamine, colorless oil.

N-Formyl-N-hydroxy-3-(3-methyl-2-pyridyl) propylamine, colorless oil.

N-Hydroxy-(2-phenoxyethyl)formamide, colorless oil.
N-Formyl-N-hydroxy-2-(3-hydroxyphenoxy)ethylamine 2a. To a solution of O-(2-Hydroxyethyl)resorcinol (4 g) and sodium hydroxide (1.04 g) dissolved in methanol (60 mL) was added benzyl bromide (4.44 g), and the resulting reaction mixture was stirred overnight. After this time, approximately 30 mL of the methanol was removed in vacuo, and the mixture was diluted with methylene chloride (100 mL). The organics were washed with water and aqueous 1N NaOH, dried, and concentrated to provide 2-(3-benzyloxyphenoxy)ethanol (5.03 g).

2b. To a solution of 2-(3-benzyloxyphenoxy)ethanol (5.03 g) and tert-butyl N-(tert-butoxycarbonyloxy)carbamate (4.81 g) in dry THF was added triphenylphosphine (5.40 g), followed by diisopropyl azodicarboxylate (4.16 g). The reaction solution was stirred for 1 h, and then most of the THF was removed in vacuo. The resulting residue was purified by flash chromatography (10% ethyl acetate/hexanes) to provide the di-protected hydroxylamine (7.47 g).

2c. A solution of the above protected hydroxylamine (4.5 g) in 2:1 $CH_2Cl_2$:TFA (45 mL) was stirred for 1 h. The solvents were removed in vacuo, and the resulting residue was twice dissolved in dichloroethane and concentrated in order to remove additional TFA. Then the residue was dissolved in $CH_2Cl_2$ and washed with aq. sat. $NaHCO_3$. The organics were dried and concentrated to provide the hydroxylamine (2.5 g) as a pale peach oil.

2d. A solution of acetic anhydride (0.36 mL) and formic acid (0.16 mL) was allowed to stand at 50° C. for one hour. After cooling, this mixed anhydride was added to a solution of the above hydroxylamine (1.0 g) and triethylamine (0.59 mL) in $CH_2Cl_2$. After stirring for 30 min, the reaction was extractively purified using additional $CH_2Cl_2$ and water. The organics were dried and concentrated, and the residue was purified by reverse-phase HPLC to provide N-formyl-N-hydroxy-2-(3-benzyloxyphenoxy)ethylamine (300 mg), as a colorless oil.

Proceeding in a similiar manner (examples 2b–2d), but substituting appropriate intermediates for those described above, the following compounds were made:

N-Formyl-N-hydroxy-2-(2,4,5-trifluorophenoxy) ethylamine, colorless oil.

N-Formyl-N-hydroxy-2-(2-chlorophenoxy)ethylamine, colorless oil.

2e. A heterogeneous solution of N-formyl-N-hydroxy-2-(3-benzyloxyphenoxy)ethylamine (300 mg) and Pd/C (100 mg) in methanol (7 mL) was stirred under an $H_2$ balloon for 3 h. The reaction mixture was then filtered through Celite, washing with $CH_2Cl_2$. The filtrate was concentrated to a yellow oil which was purified by reverse-phase HPLC to provide N-formyl-N-hydroxy-2-(3-hydroxyphenoxy) ethylamine as a white solid.

General Procedure for Solid-phase Synthesis of N-formyl-N-hydroxylamine Ethers

Following the procedures outlined in Example 1(a–c), t-butyldimethylsilyloxyacetaldehyde is transformed into the hydroxylamine (3-Scheme-3). Treatment of the hydroxylamine with 1 equivalent of the mixed anhydride prepared from formic acid and acetic anhydride (1:1) and 1 equivalent of triethylamine in dichloromethane provides the N-formyl-N-hydroxylamine as shown in 4-Scheme-3. Loading of the N-formyl-N-hydroxylamine onto resin is accomplished by shaking a solution of 2-chlorotrityl resin, the N-formyl-N-hydroxylamine, and triethylamine in dichloromethane overnight. The resin is then washed with dichloromethane, tetrahydrofuran, and again with dichloromethane. Treatment of the loaded resin with TBAF in THF and shaking for 3 hours, followed by washing with tetrahydrofuran, dichloromethane, methanol, and again with dichloromethane, provides the free alcohol on the resin. Treatment of the alcohol with the appropriate aromatic alcohol under Mitsunobu conditions (DIAD, PPh3, THF) overnight, followed by washing with tetrahydrofuran (3 times), dichloromethane, DMF, tetrahydrofuran, and dichloromethane, provides the aromatic ethers as in 7-Scheme-3. Cleavage of the products from support is accomplished by treating the resin with a solution of 5% TFA in methanol for 15 min, followed by washing with dichloromethane then methanol. The filtrate is then concentrated and purified by high-throughput reverse-phase HPLC to provide the ethers such as 8-Scheme-3.

According to this procedure, the following compounds were prepared:

N-Formyl-N-hydroxy-2-(2-trifluoromethylphenoxy) ethylamine, white solid.

N-Formyl-N-hydroxy-2-(7-quinolinoxy)ethylamine, colorless oil.

N-Formyl-N-hydroxy-2-(3-bromophenoxy)ethylamine, white solid.

N-Formyl-N-hydroxy-2-(2-benzyloxyphenoxy) ethylamine, white solid.

N-Formyl-N-hydroxy-2-(3-chloro-4-fluorophenoxy) ethylamine, white solid.

N-Formyl-N-hydroxy-2-(3,5-dichlorophenoxy) ethylamine, white solid.

N-Formyl-N-hydroxy-2-(2,3-dichlorophenoxy) ethylamine, white solid.

N-Formyl-N-hydroxy-2-[4-(3-methylpropionate) phenoxy]ethylamine, white solid.

N-Formyl-N-hydroxy-2-(4-acetylphenoxy)ethylamine, white solid.
N-Formyl-N-hydroxy-2-(5-isoquinolinoxy)ethylamine, colorless oil.
N-Formyl-N-hydroxy-2-(4-chloro-3-methylphenoxy)ethylamine, white solid.
N-Formyl-N-hydroxy-2-(3-chloro-4-methylphenoxy)ethylamine, white solid.
N-Formyl-N-hydroxy-2-(napthalen-1-yloxy)ethylamine, white solid.
N-Formyl-N-hydroxy-2-(napthalen-2-yloxy)ethylamine, white solid.

What is claimed is:

1. A compound according to formula (I):

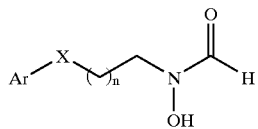
(I)

wherein:

X is O;

n is an integer 1 or 2;

Ar is an aryl group selected from the group consisting of azaindolyl, pyrazinyl, isoxazolyl, oxazolyl, thiazolyl, isothiazolyl, imidazolyl and isoquinolinyl;

such that Ar may be optionally substituted with one, two, or three substituents selected from the group consisting of optionally substituted alkyl or cycloalkyl of one to nine carbons, halo, alkoxy of one to nine carbons, hydroxy, amino, hydroxyalkyl of one to nine carbons, alkoxyalkyl, wherein the alkyl and alkylene groups are independently of one to nine carbons, optionally substituted aryl or optionally substituted heteroaryl, carboxy, and alkoxycarbonyl.

2. A compound according to claim 1 wherein Ar is 5-Isoquinoline.

3. A compound according to claim 1 which is: N-Formyl-N-hydroxy-2-(5-isoquinolinoxy)ethylamine.

* * * * *